United States Patent
Shin et al.

(10) Patent No.: US 11,920,026 B2
(45) Date of Patent: Mar. 5, 2024

(54) POLYMER, PREPARATION METHOD THEREFOR, NANOFIBER SYNTHESIZED THEREFROM, AND METHOD FOR FABRICATING SAME NANOFIBER

(71) Applicant: i-CoreBio Inc., Seoul (KR)

(72) Inventors: Jae Ho Shin, Seoul (KR); Ki Hak Gwon, Seoul (KR)

(73) Assignee: I-Corebio Inc. (KR)

( * ) Notice: Subject to any disclaimer, the term of this patent is extended or adjusted under 35 U.S.C. 154(b) by 651 days.

(21) Appl. No.: 16/845,636

(22) Filed: Apr. 10, 2020

(65) Prior Publication Data
US 2020/0325307 A1    Oct. 15, 2020

(30) Foreign Application Priority Data

Apr. 10, 2019  (KR) ................ 10-2019-0042133
Mar. 16, 2020  (KR) ................ 10-2020-0032057

(51) Int. Cl.
| | | |
|---|---|---|
| C08L 5/08 | (2006.01) | |
| A61L 31/04 | (2006.01) | |
| A61L 31/14 | (2006.01) | |
| A61L 31/16 | (2006.01) | |
| D01D 1/02 | (2006.01) | |
| D01D 5/00 | (2006.01) | |
| D01D 5/38 | (2006.01) | |
| B82Y 30/00 | (2011.01) | |
| C08B 37/08 | (2006.01) | |

(52) U.S. Cl.
CPC .............. *C08L 5/08* (2013.01); *A61L 31/042* (2013.01); *A61L 31/148* (2013.01); *A61L 31/16* (2013.01); *D01D 1/02* (2013.01); *D01D 5/0015* (2013.01); *D01D 5/38* (2013.01); *A61L 2300/114* (2013.01); *A61L 2400/12* (2013.01); *B82Y 30/00* (2013.01); *C08B 37/0072* (2013.01); *C08L 2201/06* (2013.01); *C08L 2203/12* (2013.01)

(58) Field of Classification Search
CPC ........ A61L 31/042; A61L 31/16; A61L 31/06; A61L 2300/114; A61L 2400/12; C08L 5/08; C08L 2201/06; C08L 2203/12; B82Y 30/00

USPC .......................................................... 536/55.3
See application file for complete search history.

(56) References Cited

U.S. PATENT DOCUMENTS

| | | | |
|---|---|---|---|
| 7,279,176 B1 * | 10/2007 | West ................. | A61K 31/00 424/426 |
| 8,394,393 B2 * | 3/2013 | Mather ............... | D06M 15/643 977/788 |

FOREIGN PATENT DOCUMENTS

KR    10-2014-0110360 A    9/2014

OTHER PUBLICATIONS

Damodaran et al, J. Mater. Chem., 2012, 22, 5990.*
Lu et al, Biomaterials, 2014, 35, 1716-1724.*
Gwon et al., "Biodegradable Nitric Oxide (NO) Storage and Delivery Hyaluronic Acid-Based Nanofibers: Potent Applications for Tissue Engineering and Regenerative Medicine," Materials Research Society Presentation, (Nov. 29, 2018).
Damodaran et al., "S-Nitrosated biodegradable polymers for biomedical applications: synthesis, characterization and impact of thiol structure on the physicochemical properties," Journal of Materials Chemistry, 22(13): 5990-6001 (2012).
Extended European Search Report for EP Application No. 20168932.0 dated Feb. 25, 2021.

* cited by examiner

*Primary Examiner* — Ganapathy Krishnan
(74) *Attorney, Agent, or Firm* — FOLEY HOAG LLP

(57) ABSTRACT

Disclosed herein is a novel polymer having a structure based on a biodegradable polymer. In the novel polymer, the biodegradable polymer has at least one kind of functional groups from among a hydroxyl group and a carboxyl group, wherein the biodegradable polymer bears a functional group conjugated with a nitric oxide-releasing compound and a different functional group substituted with a photopolymerizable functional group, the nitric oxide-releasing compound comprising a NO donor. Also provided is a nanofiber fabricated from the modified biodegradable polymer. The nanofiber can be fabricated by electrospinning the novel polymer.

9 Claims, 11 Drawing Sheets
(11 of 11 Drawing Sheet(s) Filed in Color)

POLYMER, PREPARATION METHOD THEREFOR, NANOFIBER SYNTHESIZED THEREFROM, AND METHOD FOR FABRICATING SAME NANOFIBER

BACKGROUND OF THE INVENTION

1. Field of the Invention

Various embodiments of the present disclosure pertain to a novel polymer, a preparation method therefor, a nanofiber synthesized from the polymer, and a method for fabricating the same nanofiber. More specifically, various embodiments of the present disclosure pertain to a polymer having a novel structure, and a nanofiber manufactured using the same and capable of storing and transferring nitric oxide, and a fabricating method therefor.

2. Description of the Prior Art

Nitric oxide (NO) is known to play a very important role in a variety of biological processes including vasodilation, neurotransmission, angiogenesis, phagocytosis, wound healing, thrombosis prevention, protection of myocardial injury, immune reaction, etc. For example, the antithrombotic characteristics of the vascular surface are attributed mainly to the nitric oxide produced in the endothelial cells of the blood vessel inner wall. Nitric oxide produced in the inner wall inhibits the activation and aggregation of platelets by controlling the flow and pressure of blood. Furthermore, nitric oxide produced in phagocytes fights against micro-organic materials, such as bacteria penetrated into the body. Since nitric oxide facilitates vasodilation or angiogenesis in addition to these characteristics, nitric oxide is effective in the treatment of wounds, particularly skin that has been burned, and may also prevent bacteria from entering the wound to reduce the risk of infections.

Thanks to the finding that nitric oxide plays an important role in physiological processes, active research is also ongoing on techniques for not only stably storing nitric oxide in a material, but also exactly transferring nitric oxide to a target site. Various materials capable of storing and transferring nitric oxide have been reported. Nitric oxide may be stored in various materials ranging from small molecules to dendrimers, liposomes, nanoparticles, carbon nanotubes, porous particles, and micelles according to the use.

As such, many nitric oxide storing materials exist. However, indeed, there are not so many materials that can be directly applied to the living body. Among materials able to or likely to store and transfer nitric oxide, it is a nanofiber that is sufficiently biocompatible enough to exhibit good effects in the medical field. Having a structure which resembles the in vivo network structure in morphology, nanofibers have been studied and reported to guarantee excellent results upon cell culturing. In fact, nanofibers tend to be the norm. Due to the poor productivity thereof, nanofibers had not been widely used in the industrial field. Since the mid-1990s when electrospinning devices available for the production of nanofibers were successfully simplified, intensive attention has been paid to nanofibers.

Electrospinning processes are simpler than other production technologies in aspect of the device used therefor and enable even a small amount of most polymer solutions or melts to be spun. For this reason, studies have been actively conducted into the provision of various structures and functionalities. Collaboration between nanofibers that have many advantages and nitric oxide, which is responsible for essential functions in vivo and has been verified for the artificial availability thereof, could result in maximizing such advantageous features. Studies on nanofibers capable of storing and transferring nitric oxide still remain in the initial stage, with no extensive research reports issued. However, it is expected that much research data will be actively reported in the future.

As for nanofibers, which guarantee good effects thanks to high biocompatibility among substances able or likely to store or transfer nitric oxide, there are reports as follows.

First, a polymer that forms a siloxane bridge (Si—O—Si) with aminoalkoxysilane for storing nitric oxide in the form of N-diazeniumdiolate through reaction with amines is subjected to a sol-gel reaction and then electrospun into nanofibers (Korean Patent No. 10-2014-0110360 A). However, the process of storing nitric oxide in aminoalkoxysilane requires the application of the toxic nitric oxide gas at a high pressure of 5-10 atm for three days, which is dangerous and time consuming. In addition, heat or $H^+$ causes the N-diazeniumdiolate-based NO donor to releases nitric oxide. In this regard, too much nitric oxide is released in the initial stage. Thus, when applied in vivo, the donor may generate cytotoxicity. Furthermore, since the primary amine group contained in the aminoalkoxysilane takes toxicity, the polymer left after release of nitric oxide may be per se toxic.

Next, small molecules or dendrimers entrapping nitric oxide therein are physically mixed with an electrospinnable polymer which is then prepared into nanofibers (Worley, B. V.; Soto, R. J.; Kinsley, P. C.; Schoenfisch, M. H. ACS Biomaterial 2016, 2, 426-437. and Koh, A.; Carpenter, A. W.; Slomberg, D. L.; Schoenfisch, M. H. ACS Appl. Mater. Interfaces 2013, 5, 7956-7964.). However, the nitric oxide-entrapping moieties in the nanofibers can be readily extricated from the nanofibers and there are no ideas on what side effects may be caused by the extricated nitric oxide-entrapping moieties in vivo.

A method in which a polymer is melt and spun into nanofibers, followed by storing nitric oxide therein is suggested (Lowe, A.; Deng, W.; Smith, D. W.; Balkus, K. J. ACS Macromolecules 2012, 45, 5894-5900). In this method, however, spinning is impossible, with nitric oxide being stored. In addition, after being prepared, the nanofibers must be exposed to a high pressure of nitric oxide gas for a long period of time. Thus, because nitric oxide is not stored deep in the nanofiber, but on the surface only, the polymer is lower in the storage efficiency of nitric oxide, compared to the polymer in which nitric oxide is stored prior to spinning.

Finally, there is a method in which nitric oxide is entrapped into a polymer having a SH group pendent, followed by spinning the polymer into nanofibers (Damodaran, V. B.; Joslin, J. M.; Wold, K. A.; Lantvita, S. M.; Reynolds, M. M. *J. Mater. Chem.* 2012, 22, 5990). However, it is difficult to control the storage amount and release profile of nitric oxide because the amount of nitric oxide stored in the polymer varies depending on the degree of polymerization or composition of thee polymer per se.

SUMMARY OF THE INVENTION

Various embodiments of the present disclosure provide a polymer having a novel structure for a nanofiber highly biodegradable and capable of controlling storage and release amounts of nitric oxide, a preparation method therefor, a nanofiber fabricated therefrom, and a method for fabrication of the same nanofiber.

The polymer having a novel structure according to the present disclosure is based on a biodegradable polymer.

The polymer having a novel structure according to the present disclosure may be a biodegradable polymer bearing at least one kind of a hydroxyl group and a carboxyl group, in which a functional group is conjugated with a nitric oxide-releasing compound and another functional group is substituted with a photopolymerizable functional group.

Nanofibers according to various embodiments of the present disclosure may be nanofibers modified from a biodegradable polymer.

In detail, the nanofibers according to various embodiments of the present disclosure may be fabricated by electrospinning the polymer having a novel structure.

According to various embodiments of the present disclosure, a nanofiber that is of high biocompatibility and is capable of controlling the storage amount and release amount of nitric oxide can be provided. In detail, the nanofibers according to various embodiments of the present disclosure can control a payload of nitric oxide in the wide range of from 5 nmol·mg$^{-1}$ to 5,000 nmol·mg$^{-1}$. In addition, nanofibers according to various embodiments of present disclosure are free of cytotoxicity and as such, can reduce potential toxicity when applied in vivo.

Being of high biodegradability at various concentrations of hyaluronidase (HAse) measured in the practical biological system, the nanofibers according to various embodiments can be applied to various sites in vivo. In addition, the nanofibers according to various embodiments of the present disclosure promotes cell migration to promote wound healing, thereby finding applications in various regenerative medicine fields including burn treatment, renal transplantation, etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
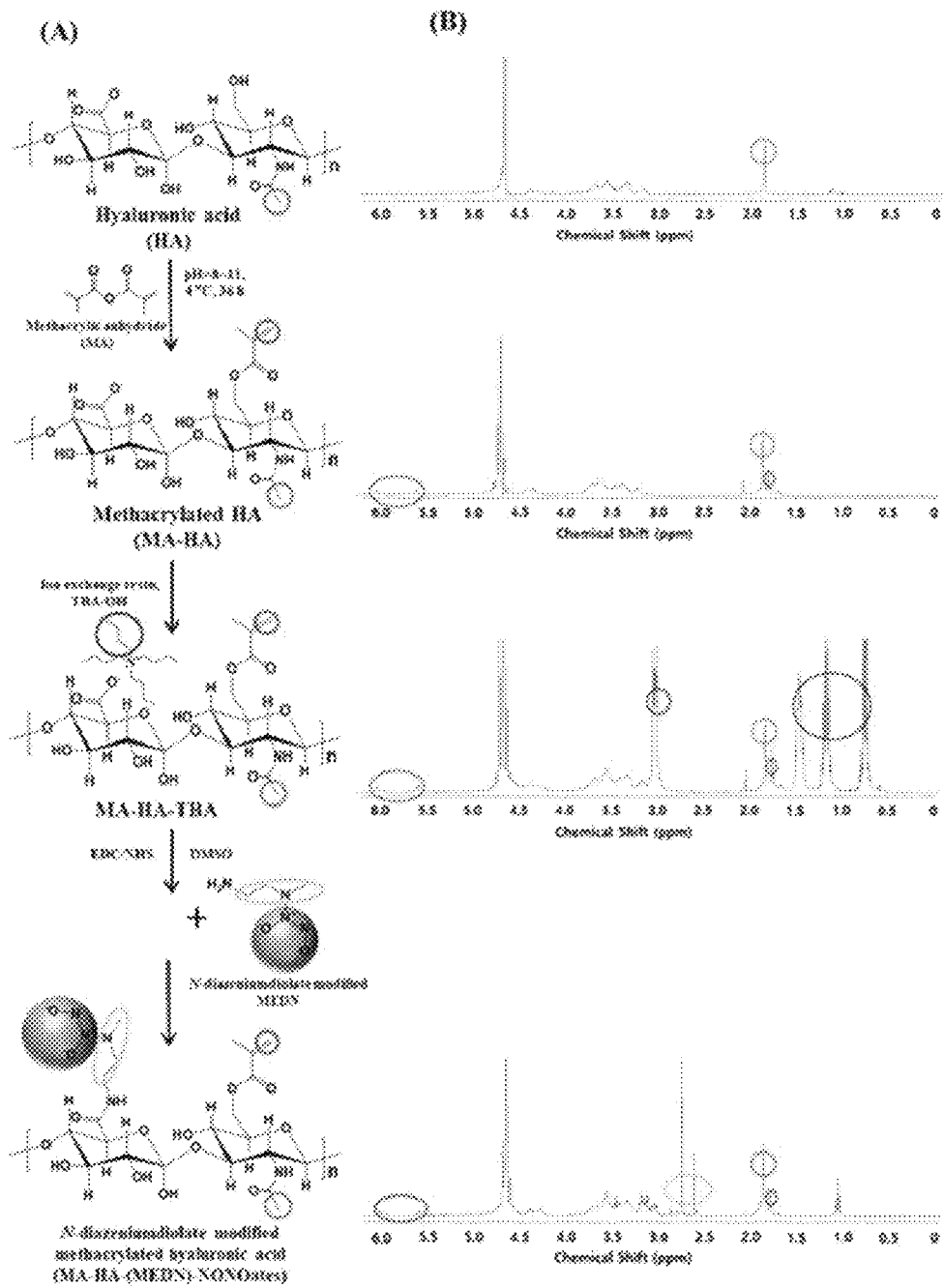
FIG. 1 shows a schematic view of the preparation method of polymers according to various embodiments of the present disclosure (A), along with proton NMR data thereof (B)

Hereinafter, various embodiments of this document will be described. Embodiments and terms used herein are not intended to limit the technologies described in the present disclosure to specific embodiments, and it should be understood that the embodiments and the terms include modifications, equivalents, and/or alternatives on the corresponding embodiments described herein.

Polymer Having Novel Structure and Preparation Method Therefor

A polymer according to various embodiments of the present disclosure is based on a biodegradable polymer having at least one functional group among from a hydroxyl group and a carboxyl group.

The biodegradable polymer may be a natural polymer such as hyaluronic acid, gelatin, starch, chitin, cellulose, alginate, collagen, heparin, or chitosan, or a synthetic polymer such as polylactic acid (PLA), polyglycolic acid (PGA), poly(lactic-co-glycolic acid) (PLGA), polycaprolactone (PCL), polydioxanone (PDO), poly(trimethylenecarbonate) (PTMC), or polyhydroxyalkanoate (PHA).

In detail, a polymer according to various embodiments of the present disclosure bears at least one kind of a hydroxyl group and a carboxyl group, in which one functional group is conjugated with a nitric oxide-releasing compound and another functional group is substituted with a photopolymerizable functional group.

For example, when the biodegradable polymer bears both a hydroxyl group and a carboxyl group, the carboxyl group may be conjugated with a nitric oxide-releasing compound while the hydroxyl group may be substituted with a photopolymerizable function group. The biodegradable polymer bearing both a hydroxyl group and a carboxyl group may be, by way of example, hyaluronic acid. Hyaluronic acid has the following chemical formula.

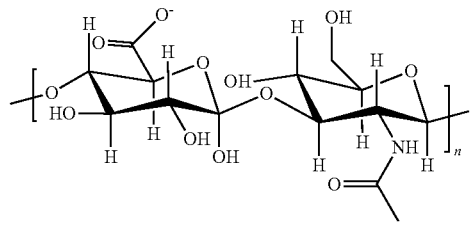

Hyaluronic acid has biocompatibility, hydrophobicity, and biodegradability and is involved in the cytological processes of proliferation, inflammation, and wound healing. In addition, hyaluronic acid is rich in hydroxyl and carboxylic groups and as such, can be readily modified with various functional groups.

In an alternative, when biodegradable polymer bears hydroxyl groups only, a part of the hydroxyl groups may be substituted with a carboxyl group which is then conjugated with a nitric oxide-releasing compound while another part of the hydroxyl groups may be substituted with a photopolymerizable functional group. Examples of the biodegradable polymer bearing hydroxyl groups only include starch, chitin, and chitosan.

include gelatin, alginate, heparin, polylactic acid (PLA), polyglycolic acid (PGA), poly(lactic-co-glycolic acid) (PLGA), poly(trimethylenecarbonate) (PTMC), polydioxanone (PDO), and polyhydroxyalkanoate (PHA).

Gelatin has the following chemical formula.

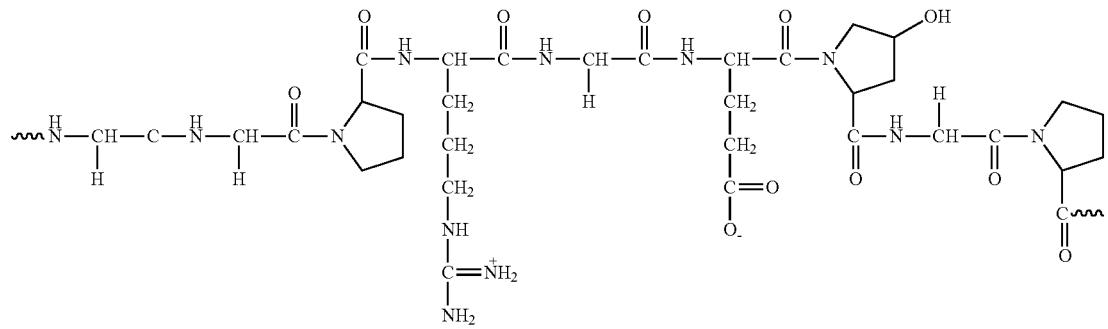

Starch has the following chemical formula.

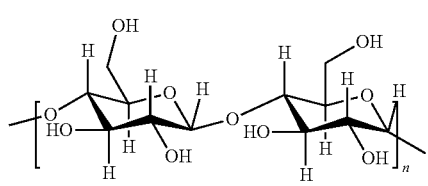

Chitin has the following chemical formula.

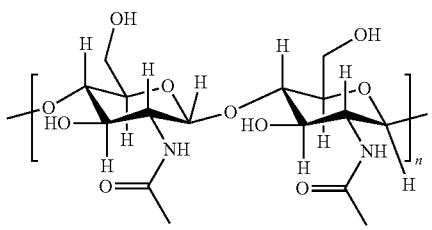

Chitosan has the following chemical formula.

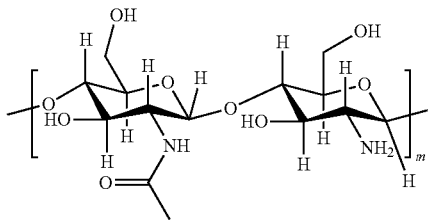

In another alternative, when the biodegradable polymer bears carboxylic groups only, a part of the carboxylic groups may be conjugated with a nitric oxide-releasing compound while another part of the carboxylic groups may be substituted with a hydroxyl group which is then substituted with a photopolymerizable functional group. Examples of the biodegradable polymer bearing carboxylic groups only Alginate has the following chemical formula.

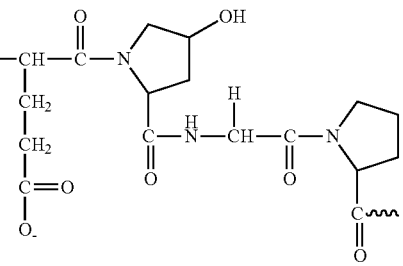

Heparin has the following chemical formula.

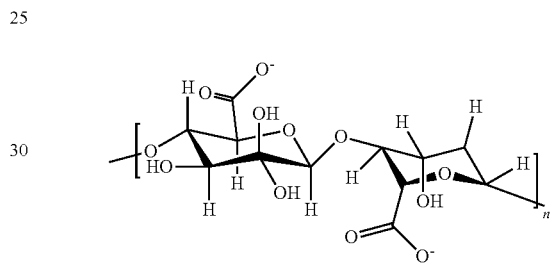

PLA has the following chemical formula.

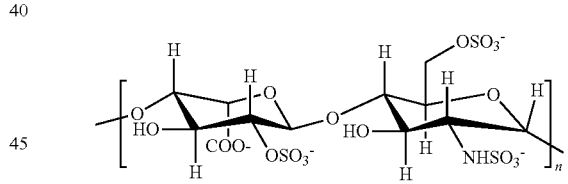

PGA has the following chemical formula.

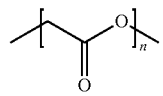

PLGA has the following chemical formula.

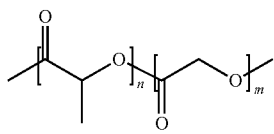

PTMC has the following chemical formula.

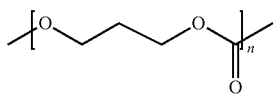

PDO has the following chemical formula.

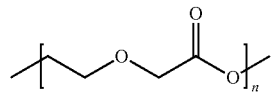

PHA has the following chemical formula.

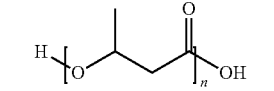

Meanwhile, the photopolymerizable functional group may include at least one selected from the group consisting of: a methacrylate, ethacrylate, crotonate, cinnamate, vinyl ether, vinyl ester, ethenylarylene, dicyclopentadienyl, norbornenyl, isoprenyl, isopropenyl, allyl, or butenyl group; an ethenylarylene ether, dicyclopentadienyl ether, norbornenyl ether, isoprenyl ether, isopropenyl ether, allyl ether, or butenyl ether group; and an ethenylarylene ester, dicyclopentadienyl ester, norbornenyl ester, isoprenyl ester, isopropenyl ester, allyl ester, butenyl ester, or glycidyl methacrylate group. In other words, the photopolymerizable functional group contains an unsaturated double bond.

The nitric oxide-releasing compound may be a substance that can store nitric oxide and release the same in a specific condition. For example, the nitric oxide-releasing compound may a compound including a NO donor.

In this regard, the NO donor may include at least one selected from the group consisting of organic nitrites, organic nitrates, nitrosothiols, C-nitroso compounds, N-hydroxyl nitrosamine, diazetine dioxides, oxatriazole-5-imine, N-nitrosamines, sydnonimines, oximes, hydroxylamines, N-hydroxyguanidines, hydroxyurea, nitrosiamine, N-hydroxyl nitrosamines, NO-metal complexes, and N-diazeniumdiolates (NONOates).

By way of example, representative NO donors may have the following chemical formulas.

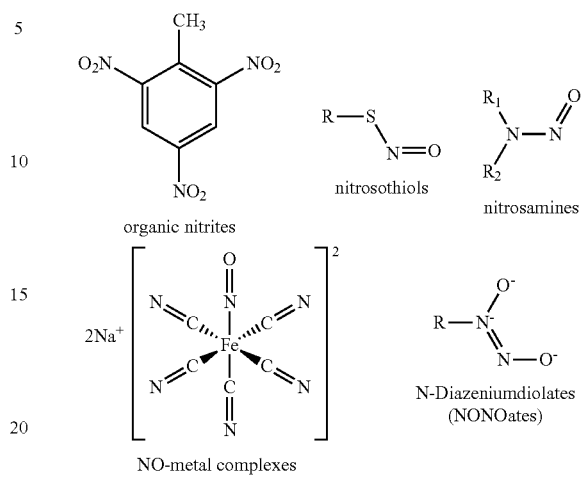

When including the NO donor NONOates, the nitric oxide-releasing compound can release nitric oxide through the following process. That is, it is decomposed in an aqueous solution condition to release nitric oxide.

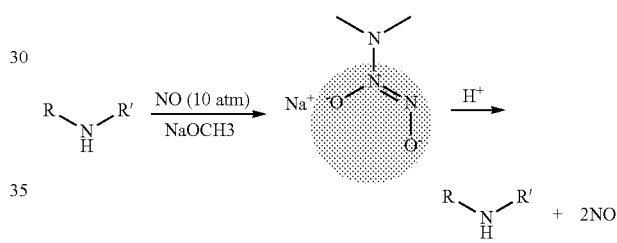

Meanwhile, the amine compound may include at least one selected from the group consisting of N-methylethylendiamine(N-MEDN), N-ethylethylenediamine(N-EEDN), N-isopropylethylenediamine(N-IPED), N-isopropyl-1,3-propanediamine(N-IPPDN), and N-benzylethylenediamine (N-BEDN).

According to an embodiment of the present disclosure, the nitric oxide-releasing compound may be modified from the amine compound and include N-diazeniumdiolates (NONOates) among the NO donors. For example, the nitric oxide-releasing compound may include at least one selected from the group consisting of (MEDN)-NONOates, which is modified from N-MEDN, (EEDN)-NONOates, which is modified from N-EEDN, (IPED)-NONOates, which is modified from N-IPED, (IPPDN)-NONOates, which is modified from N-IPPDN, and (BEDN)-NONOates, which is modified from N-BEDN.

Preferably, the nitric oxide-releasing compound may be (MEDN)-NONOates, which is modified from N-methylethylendiamine (N-MEDN). In this regard, (MEDN)-NONOates may have the following chemical formula.

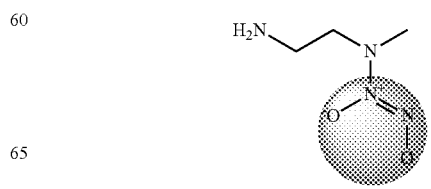

The polymers according to various embodiments of the present disclosure, a polymer with hyaluronic acid serving as a backbone may have the following chemical formula:

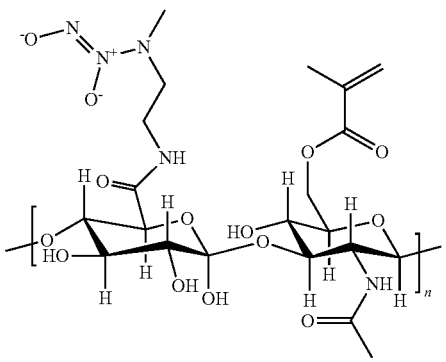

wherein n is 1 or more.

With reference to the chemical formula, the hydroxyl groups in hyaluronic acid are substituted with a methacryl group while the carboxylic groups are conjugated with (MEDN)-NONOates.

Below, a description will be given of a method for preparation of polymers according to various embodiments. The method for preparation of polymers may comprise the steps of: synthesizing an intermediate; generating intermediate salt; and mixing the intermediate with a solvent and a nitric oxide-releasing compound.

In the step of synthesizing an intermediate, a biodegradable polymer is reacted with a polymer bearing a photopolymerizable functional group to substitute the photopolymerizable functional group for at least one kind of functional groups of the biodegradable polymer.

For example, when the biodegradable polymer bears both a hydroxyl group and a carboxyl group, the hydroxyl group may be substituted with a photopolymerizable functional group.

In one alternative, when the biodegradable polymer bears hydroxyl groups only, a part of the hydroxyl groups may be substituted with a photopolymerizable functional group.

In another alternative, when the biodegradable polymer bears carboxylic groups only, a part of the carboxylic groups may be substituted with a photopolymerizable functional group.

According to an embodiment, hyaluronic acid, which is a biodegradable polymer, is reacted with a polymer having a photopolymerizable functional group to substitute the photopolymerizable functional group for at least one hydroxyl group of hyaluronic acid. For example, referring to FIG. 1(A), hyaluronic acid is reacted with methacrylic anhydride to substitute the hydroxyl group of hyaluronic acid with the photopolymerizable methacrylic group to synthesize methacryl hyaluronic acid (MA-HA). That is, the hydroxyl group of hyaluronic acid is substituted with a methacryl group through transesterification to afford methacryl hyaluronic acid (MA-HA). The reaction may be conducted while the pH is maintained to be 8 to 11. In addition, after completion of the reaction, purification may be carried out through precipitation, centrifugation, and dialysis.

Subsequent to the step of synthesizing an intermediate, a step of generating an intermediate salt may be conducted. This is a pre-treatment step for solubilizing the intermediate in an organic solvent. For example, with reference to FIG. 1(A), the intermediate MA-HA can be converted into a tetrabutyl ammonium (TBA) salt (MA-HA-TBA) using an ion exchange resin. This pretreatment step is necessary because the final polymer synthesis should be conducted in an organic solvent due to the high decomposability of the nitric oxide-releasing compound to aqueous solutions.

In the mixing step, the intermediate salt is mixed with a solvent and a nitric oxide-releasing compound.

In this regard, when the biodegradable polymer bears both a hydroxyl group and a carboxyl group, the carboxyl group may be conjugated with the nitric oxide-releasing compound.

Alternatively, when the biodegradable polymer bears hydroxyl groups only, the hydroxyl groups that remain unsubstituted in the previous intermediate synthesis step may be beforehand converted into carboxylic groups which are then conjugated with a nitric oxide-releasing compound.

Further alternatively, when the biodegradable polymer bears carboxylic groups only, the carboxylic groups that remain unsubstituted in the previous intermediate synthesis step may be conjugated with a nitric oxide-releasing compound.

In a particular embodiment, the nitric oxide-releasing compound may be MEDN-NONOates. The intermediate salt (MA-HA-TBA) and the nitric oxide-releasing compound may be in a molar ratio of 1:0.5 to 1:30. In detail, the molar ratio of the intermediate salt (MA-HA-TBA) and the nitric oxide-releasing compound may be 1:2, 1:5, or 1:7. When fabricated from the polymers using such molar ratios, the nanofibers for storing and releasing nitric oxide can store and release a various concentration range of nitric oxide, with the release time optimized.

With reference to FIG. 1(A), when the biodegradable polymer is hyaluronic acid, carboxylic groups of hyaluronic acid may be conjugated with the nitric oxide-releasing compound through the mixing step.

According to applications of the polymers of the present disclosure, the molar ratio of biodegradable polymer and nitric oxide-releasing compound may be variously adjusted. For example, the degradation rate of the nanofiber can be controlled by adjusting a content of the biodegradable polymer. On the other hand, the release amount of nitric oxide can be controlled by adjusting a content of the nitric oxide-releasing compound. The release amount of nitric oxide may vary depending on the content of the nitric oxide-releasing compound. The polymers of the present disclosure can find various applications according to uses thereof because it is easy to control such molar ratios.

Nanofiber for Storing and Transferring Nitric Oxide and Fabrication Method therefor Nanofibers according to various embodiments of the present disclosure may be nanofibers modified from biodegradable polymers. In detail, the polymers having novel structures described above may be electrospun into nanofibers.

Hereinafter, a method for fabrication of nanofibers according to various embodiments of the present disclosure is described.

A method for fabrication of nanofibers may comprises the steps of: preparing the aforementioned polymer having a novel structure; preparing a polymer precursor containing the polymer, an additive, and a photoinitiator; and electrospinning the polymer precursor.

The polymer precursor may be a mixture of the polymer of the present disclosure, poly(ethyleneoxide) (PEO), 4-arm poly(ethyleneglycol)-thiol (4-arm PEG-SH), a photoinitiator, and a base. In this polymer precursor mixture, the polymer may be contained at a concentration of 1 to 50%

(w/v). When fabricated from such a concentration of the polymer, the nanofibers for storage and release of nitric oxide can cover the storage and release of nitric oxide at a various concentrations, with the release time optimized therefor.

PEO may be contained in an amount of 0.1% (w/v) to 10% (w/v), based on the total weight of the polymer precursor mixture. The PEO may have a molecular weight of 1,000 to 1,000,000 g/mol.

4-arm PEG-SH may be contained in an amount of 0.1% (w/v) to 10% (w/v), based on the total weight of the polymer precursor mixture. 4-arm PEG-SH may range in molecular weight from 1,000 to 1,000,000 g/mol. Instead of 4-arm PEG-SH, either or both of linear PEG-SH and 6-arm PEG-SH may be employed.

The photoinitiator may be Irgacure 2959. Irgacure 2959 may be used at a concentration of 0.01% (w/v) to 10% (w/v).

The base may include at least one selected from the group consisting of ammonium hydroxide ($NH_4OH$), sodium methoxide (NaOMe), sodium ethoxide (NaOEt), and sodium propoxide (NaOPr). The nanofibers may vary in storage and release profiles of nitric oxide, depending on kinds and molar concentrations of the base added. In other words, in order to store and release a desired concentration range of nitric oxide, kinds and molar concentrations of the base added to the polymer precursor may be adjusted.

Figure 3:
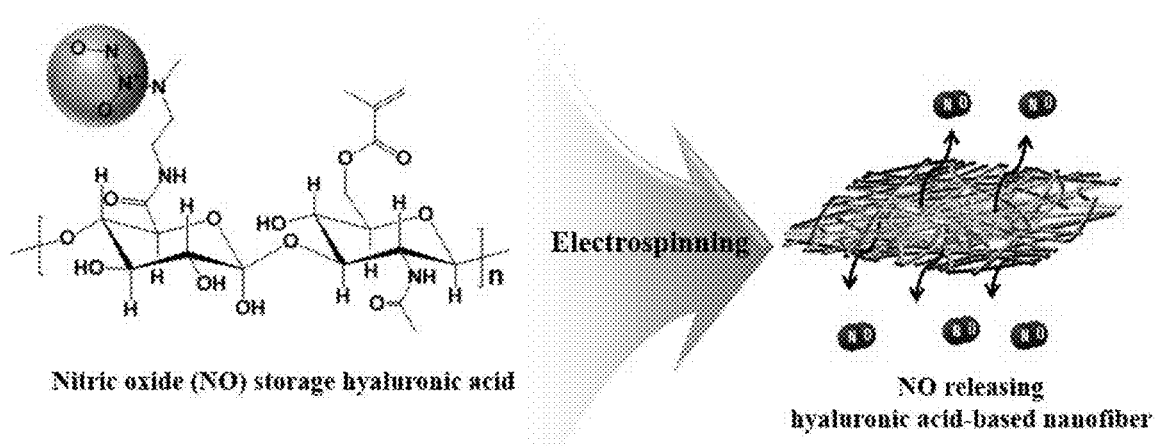
FIGS. 3 and 4 are schematic diagrams of the preparation method for nanofibers according to various embodiments of the present disclosure.
Figure 4:
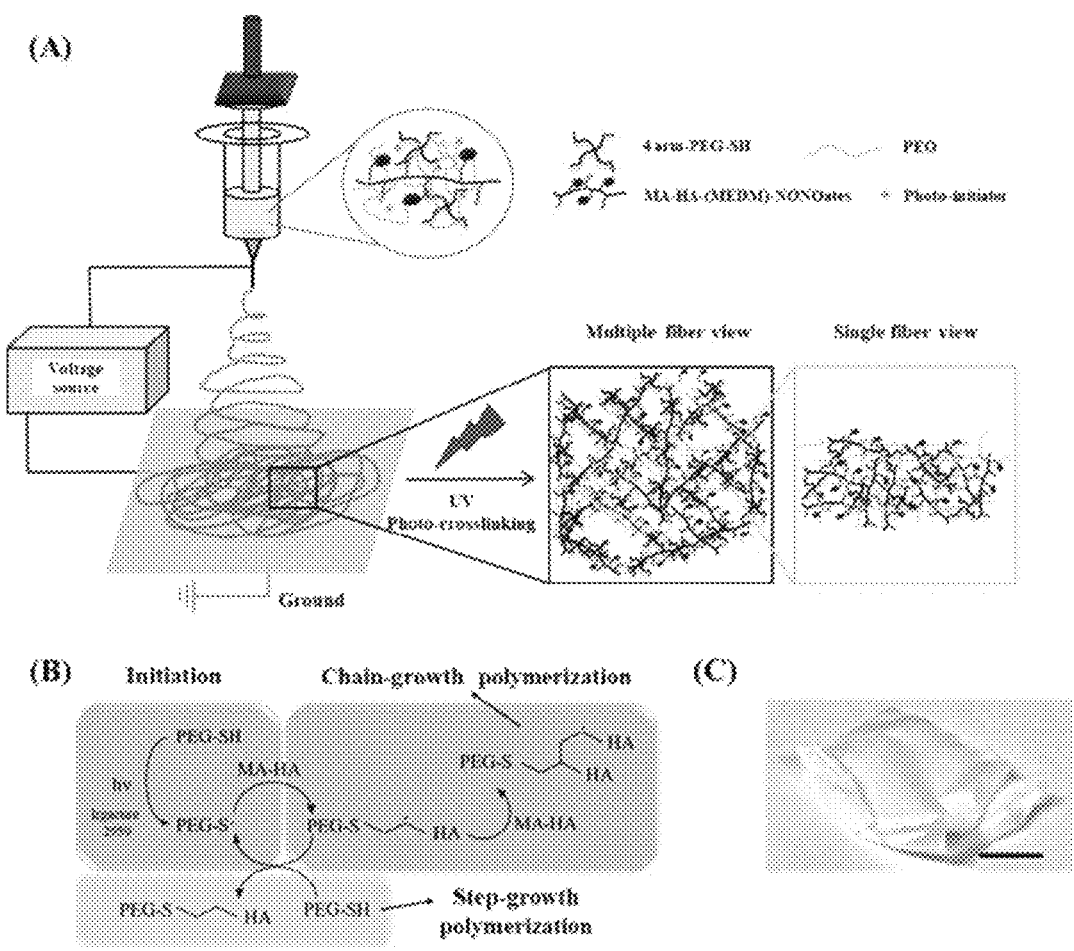

Referring to FIGS. 3 and 4, the polymer precursor can be electrospun. Electrospinning is a complicate process that may be affected by various parameters including polymer concentrations, surface tension, electric conductivity, solvents, applied voltages, flow rates, and needle gauges.

The method may further a photopolymerization step prior or subsequent to the electrospinning step. The photopolymerization step may give stability to the structure of the nanofibers.

Below, a detailed description will be given of the present disclosure with reference to Examples and Experimental Examples. However, the following Examples and Experimental Examples are set forth to illustrate, but are not to be construed as limiting the present disclosure.

EXAMPLES

Step 1. Synthesis of methacryl hyaluronic acid (MA-HA)

500 mg of hyaluronic acid (HA) (40 kDa) was dissolved in 50 mL filtered deionized water (DIW) to make a 1% (w/v) HA solution. 5-fold molar excess amount (0.931 mL) of methacrylic anhydride was added to the solution and reacted for 12 hours in the dark at 4° C. while maintaining pH between 8 to 11 using 5 N or 1 N NaOH. The final product (HA-MA→MA-HA) was precipitated in 10-time excess amounts of cold ethanol (EtOH). After centrifugation at 5,000 rpm for 5 minutes at 4° C., the supernatant was removed and the precipitate was re-dissolved in 50 mL of DIW. To remove unreacted reagents, MA-HA was purified by dialysis against DIW using a dialysis membrane (3.5 kDa Mw cut-off) for 3 days.

Step 2. Synthesis of MA-HA-TBA 15 g (75 mmol) Dowex 50WX-8-400 ion-exchange resin was suspended with 250 mL of DIW in a 500 mL round flask. Next, 29.335 mL of TBA-OH (112.5 mmol, 1.5 molar excess) was added to the Dowex resin in the round flask, followed by reaction for 30 minutes. The Dowex-TBA resin was filtered using a filter paper and a vacuum pump to remove impurities. For pH normalization, the resin was washed with a sufficient amount of DIW. Subsequently, 500 mg of the purified MA-HA in 100 mL of DIW was transferred into a 250-mL round flask to which the prepared Dowex-TBA resin (6.25 g, 5 molar excess) was poured into the MA-HA solution. After mixing for 3 hours, the product (MA-HA-TBA) thus formed was primarily filtered through filter paper and secondarily through a 0.45-μm filter to remove the Dowex resin. Thereafter, the product was lyophilized for 3 days and stored at −20° C. until further use.

Step 3. Synthesis of (MEDN)-NONOates 0.4593 mL (5.0 mmol) of N-MEDN and 0.9259 mL (5.0 mmol) of NaOMe were dissolved in 3.6148 mL of EtOH to make a total volume of 5 mL. The resulting solution was put in a closed chamber and exposed to 10 atm of NO gas for 3 days. After the chamber was purged with Ar, the solution was withdrawn from the chamber, vacuum sealed, and stored in a freezer.

Step 4. Synthesis of MA-HA-(MEDN)-NONOates 0.2 g (0.5 mmol—dimer, 1 equiv.) of MA-HA-TBA was dissolved in 20 mL of DMSO. To this solution, for example, EDC 0.221 mL (MW=155.24 $gmol^{-1}$, 1.25 mmol, 2.5 equiv.), NHS 0.1438 g (MW=115.09 $gmol^{-1}$, 1.25 mmol, 2.5 equiv.), and (MEDN)-NONOates 3.5 mL (3.5 mmol, 7 equiv.) were sequentially added and mixed at 25° C. for 3 hours. The amount of each reactant added to MA-HA-TBA can be varied to achieve the modification of the carboxylic groups of hyaluronic acid into NONOates groups. Finally, the reaction product was precipitated in an excess of diethyl ether, washed copiously with diethyl ether. MA-HA-(MEDN)-NONOates was dried for 3 hours under the cold vacuum condition to evaporate organic residues, and then stored in a sealed container at −20° C. until use.

Step 5. Synthesis of nanofibers

To synthesize nanofibers, a polymer precursor for electrospinning was prepared as follows. 2% (w/v) PEO as a blending polymer and 2% (w/v) 4-arm PEG-SH as a crosslinker were sequentially dissolved in DIW/$NH_4OH$ mixture (1:1 volume ratio). 0.1% (w/v) Irgacure 2959 as a photoinitiator was added to this resultant polymer solution, the pH of the polymer solution was adjusted to 11 using 1 N HCl and 4, 7, or 10% (w/v) MA-HA-(MEDN)-NONOates was added to the polymer precursor solution. Then, the mixed solution prepared above was loaded in a plastic syringe and flowed through a 25 Gauge needle and nanofibers were fabricated using a high voltage power source (ESR200PR2D, NanoNC Co., Seoul, Korea) as followed conditions: 20 μL·$min^{-1}$ of the volume flow rate, 17.5 kV of the applied voltage, 15 cm of tip to collector distance. After electrospinning, electrospun nanofibers were photo-crosslinked by using a UV LED light for 5 minutes, vacuum sealed, and stored in −20° C. freezer.

Experimental Example 1: Characterization of MA-HA-(MEDN)-NONOates

With reference to FIG. 1(A), hydroxyl groups of hyaluronic acid were substituted with methacryl groups through step 1 to afford methacryl hyaluronic acid (MA-HA). With reference to FIG. 1(B), methacrylate proton NMR peaks were detected at 5.6 and 6.1 ppm. In addition, methyl proton NMR peaks of N-acetyl group in HA were detected at 1.9 ppm.

In step 2, MA-HA is converted into a tetrabutyl ammonium salt (MA-HA-TBA) using ion exchange resin for solubilization in organic solvents (e.g., DMSO). Since the NONOates groups are easily decomposed in the aqueous solution, the synthesis process of MA-HA-(MEDN)-NONOates should be performed under the organic solvent condition in order to minimize NONOates decomposition.

Referring to FIGS. 1(A) and 1(B), the TBA conjugation process did not affect the modification of methacryl group as indicated by the methacrylate proton integration before and after the reaction, indicating the reliable synthesis of MA-HA-TBA. In addition, TBA proton NMR peaks appeared at 3.0 ppm and 1.5 to 0.7 ppm.

As observed in FIG. 1(B), MA-HA-MEDN-NONOates was synthesized by the coupling reaction of MA-HA-TBA with preformed MEDN-NONOate.

Figure 2:
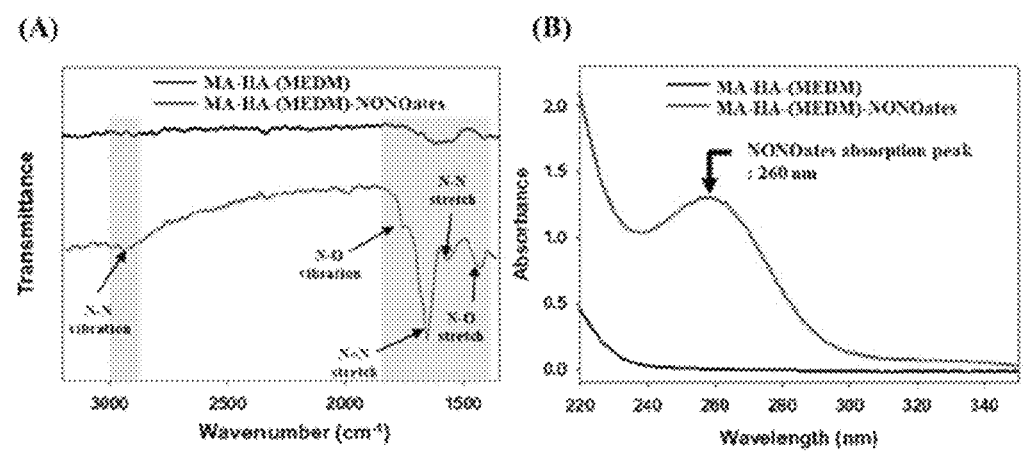
FIG. 2 shows FT-IR spectra (A) and UV-Vis spectra (B) of MA-HA-(MEDN)-NONOates.

In FIG. 2(A), the characteristic peaks of NONOates were observed in FR-IR spectroscopy. As shown in FIG. 2(B), the formation of NONOates group was confirmed via UV-Vis spectroscopy. MA-HA-(MEDN)-NONOate showed the maximum absorption at 260 nm while MA-HA-(MEDN) did not show any specific absorption peak at 260 nm. Therefore, the data demonstrates the successful synthesis of MA-HA-(MEDN)-NONOates.

Experimental Example 2: Characterization of Nanofibers

Figure 5:
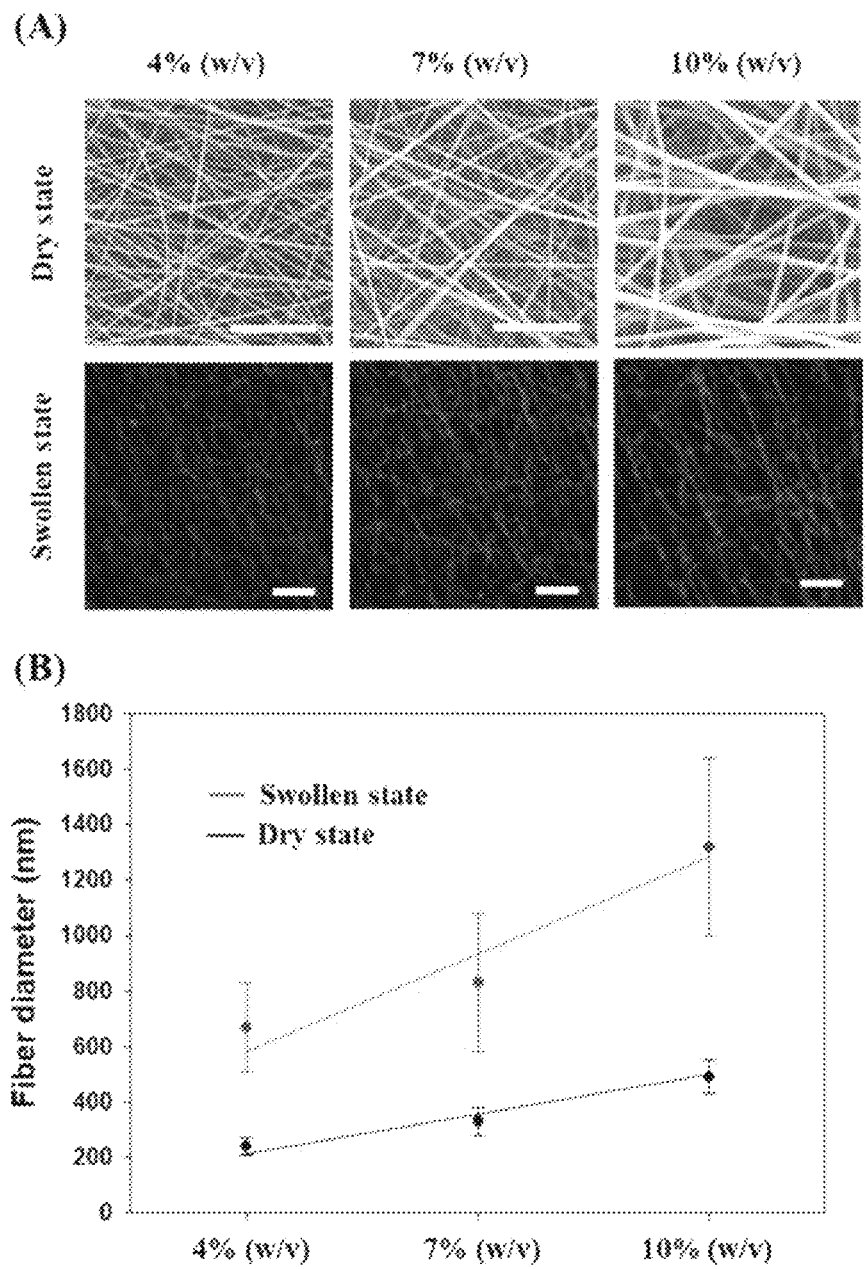
FIG. 5 shows SEM images of nanofibers in a dry state and confocal microscopic images of nanofibers in a swollen state (A) and a plot of nanofiber diameters (B)

FIG. 5(A) shows SEM images of nanofibers for dry state and confocal microscopic images of nanofibers for swollen states. From the images, fiber morphology, diameter, and swelling behaviors of the nanofibers were investigated. When the content of MA-HA-(MEDN)-NONOates was increased from 4% (w/v) to 10% (w/v) in 2% (w/v) PEO blended precursor polymer, uniform nanofibers with concentration-dependent various diameters were successfully synthesized. In FIG. 5(B), the nanofibers have average diameters of 240±30 nm, 330±50 nm, and 490±60 nm at MA-HA-(MEDN)-NONOates contents of 4% (w/v), 7% (w/v), and 10% (w/v), respectively. Therefore, the diameter of nanofibers produced by electrospinning has been found to increase with increasing MA-HA-(MEDN)-NONOates concentration. Fiber diameters of fluorescently labeled hydrated nanofibers were also measured by confocal microscopy. The distribution of fiber diameters became much wider and average diameters of 4% (w/v), 7% (w/v), and 10% (w/v) MA-HA-(MEDN)-NONOates notably increased to 670±160 nm, 830±250 nm, and 1320±320 nm, respectively. Since HA has water absorbing property, the higher the content of HA in the nanofiber, the larger the diameter of nanofiber.

Experimental Example 3: Storage and Release Profiles of Nitric Oxide

The nanofibers were evaluated for storage and release profiles of nitric oxide according to molar ratios between MA-HA and (MEDN)-NONOates and contents % (w/v) of MA-HA-(MEDN)-NONOates in the polymer precursor for electrospinning. For example, when the molar ratio between MA-HA and (MEDN)-NONOates=1:7 and 10% (w/v) MA-HA-(MEDN)-NONOates, 10% (w/v) MA-HA:(MEDN)-NONOates=1:7 was denoted.

$t[NO]$ (the total number of moles of NO release), $t_{1/2}$ (half-life of NO release), $[NO]_m$ (maximum instantaneous concentration of NO release), $t_m$ (time necessary to reach $[NO]_m$), and $t_d$ (duration of NO until NO release is finish) were evaluated. The results are summarized in Table 1, below.

FIGS. 6(A) and 6(B) depict release amounts and total release amounts of nitric oxide of representative examples with time.

TABLE 1

| Sample | MA-HA:(MEDM)-NONOate conc % (w/v)[b] | Feed molar ratio of MA-HA to (MEDM)-NONOates[c] | t[NO] (nmol · mg$^{-1}$)[d] | $t_{1/2}$ (min)[e] | $[NO]_m$ (ppb · mg$^{-1}$)[f] | $t_m$ (min)[g] | $t_2$ (h)[h] |
|---|---|---|---|---|---|---|---|
| 4% (w/v) MA-HA:MEDM-NONOates = 1:2 | 4 | | 10 ± 5 | 5.4 ± 0.6 | 160 ± 60 | 1.8 ± 0.2 | 1.5 ± 0.1 |
| 7% (w/v) MA-HA):MEDM-NONOates = 1:2 | 7 | 1:2 | 20 ± 8 | 5.4 ± 0.4 | 190 ± 20 | 2.3 ± 0.2 | 2.2 ± 0.3 |
| 10% (w/v) MA-HA):MEDM-NONOates = 1:2 | 10 | | 30 ± 7 | 5.6 ± 2.3 | 260 ± 50 | 2.3 ± 0.3 | 3.1 ± 0.5 |
| 4% (w/v) MA-HA:MEDM-NONOates = 1:5 | 4 | | 90 ± 10 | 6.4 ± 0.7 | 1340 ± 230 | 2.6 ± 0.3 | 6.2 ± 0.4 |
| 7% (w/v) MA-HA):MEDM-NONOates = 1:5 | 7 | 1:5 | 140 ± 10 | 6.9 ± 1.0 | 2150 ± 430 | 3.0 ± 0.3 | 7.1 ± 0.5 |
| 10% (w/v) MA-HA):MEDM-NONOates = 1:5 | 10 | | 170 ± 50 | 6.4 ± 1.1 | 2540 ± 750 | 3.5 ± 0.4 | 8.9 ± 1.2 |
| 4% (w/v) MA-HA:MEDM-NONOates = 1:7 | 4 | | 350 ± 10 | 7.9 ± 0.3 | 4460 ± 180 | 3.2 ± 0.2 | 11.9 ± 1.7 |
| 7% (w/v) MA-HA):MEDM-NONOates = 1:7 | 7 | 1:7 | 580 ± 50 | 8.4 ± 0.8 | 7230 ± 680 | 3.2 ± 0.2 | 15.1 ± 2.3 |
| 10% (w/v) MA-HA):MEDM-NONOates = 1:7 | 10 | | 620 ± 60 | 7.2 ± 0.8 | 8920 ± 1380 | 3.0 ± 0.2 | 20.2 ± 3.0 |

Figure 6:
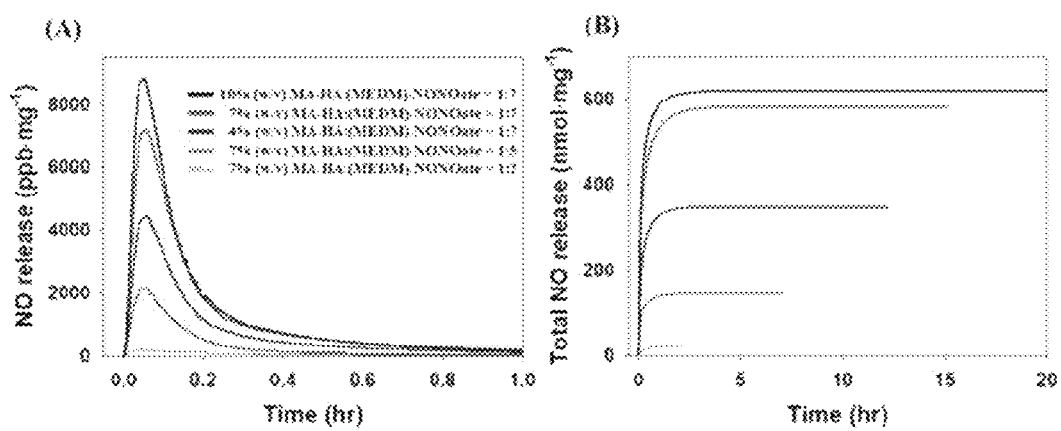
FIG. 6 shows nitric oxide flux and total amounts of nitric oxide plotted against time according to various embodiments of the present disclosure.

With reference to Table 1 and FIG. 6, nitric oxide payload of nanofibers were significantly affected by both the total MA-HA-(MEDN)-NONOate concentration in the precursor polymer and the ratio of MA-HA to (MEDN)-NONOates in synthesized MA-HA-(MEDN)-NONOates.

In detail, at a fixed MA-HA-(MEDN)-NONOates concentration of 7% (w/v), the trends of t[NO] and [NO]$_m$ were MA-HA:(MEDM)-NONOates=1:2<1:5<1:7. That is, t[NO] increased from 20 nmol·mg$^{-1}$ to 580 nmol·mg$^{-1}$ and [NO]$_m$ increased from 190 ppb·mg$^{-1}$ to 7,230 ppb·mg$^{-1}$.

In addition, at a fixed MA-HA:(MEDM)-NONOates=1:7 condition, increasing the concentration of MA-HA-(MEDM)-NONOate in precursor solution from 4 to 10% (w/v) led to notable increase in both t[NO] and [NO]$_m$. In detail, t[NO] increased from 350 nmol·mg$^{-1}$ to 620 nmol·mg$^{-1}$ and [NO]$_m$ increased from 4,460 ppb·mg$^{-1}$ to 8,920 ppb·mg$^{-1}$.

Hence, if nitric oxide-releasing nanofibers were fabricated by using either a high concentration of MA-HA-(MEDM)-NONOate (i.e., 10% (w/v)) or a high molar ratio of NONOates group in HA backbone polymer (i.e., MA-HA:(MEDN)-NONOates=1:7), the greater concentration of NONOates groups was incorporated in the fibers, resulting in the greater amount of NONOates breakdown and NO release as well as prolonged releasing time.

In various embodiments of the present disclosure, a payload of nitric oxide can be controlled within the wide range of from 5 nmol·mg$^{-1}$ to 5,000 nmol·mg$^{-1}$ by adjusting molar ratios between MA-HA and (MEDN)-NONOates and contents % (w/v) of MA-HA-(MEDN)-NONOates in the polymer precursor.

Experimental Example 4: Biodegradability Assay

Figure 7:
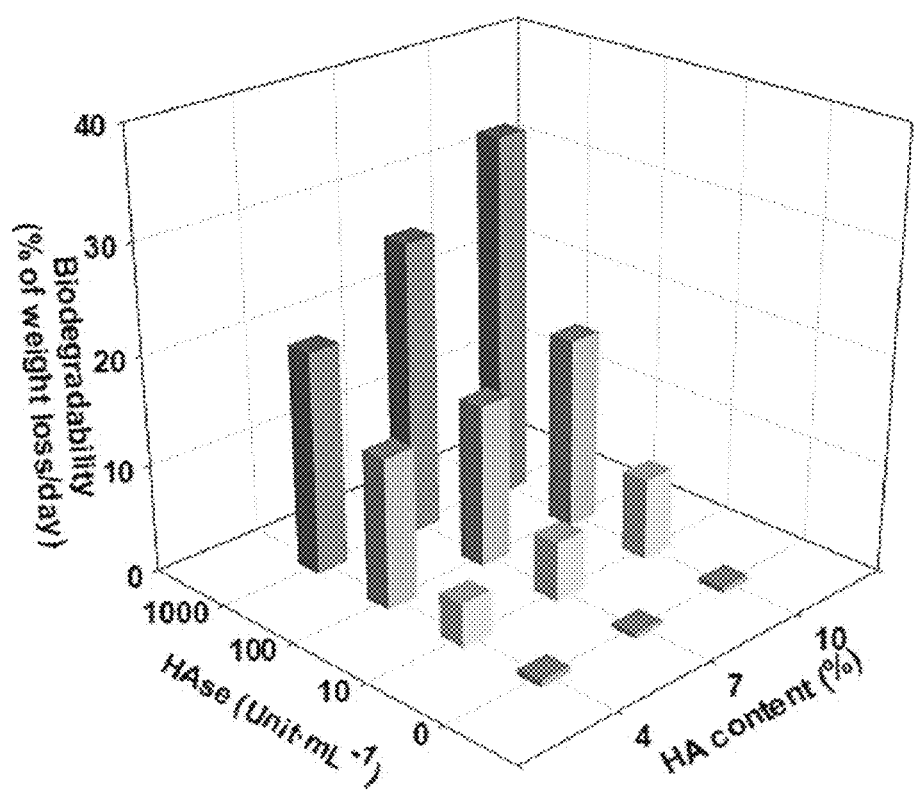
FIG. 7 shows assay results for biodegradability of nanofibers for storing or releasing nitric oxide according to embodiments.

For in vivo application, the nanofibers according to various embodiments of the present disclosure must be biodegradable. For in vivo application, implanted materials (suture, gauze or bandage-type) should be biodegradable so that a secondary surgery is not required to remove the implant. In order to evaluate the biodegradability of the nanofibers against hyaluronidase (HAse), the nanofibers were placed into PBS or HAse solutions (10-1000 U·mL$^{-1}$) and % weight loss was monitored. With reference to FIG. 7, degradation rate increased with increasing of HAse concentration. Particularly, even at the enzyme concentration of 100 U·mL$^{-1}$, which is similar to that of the practical bio-system, excellent biodegradability was detected, indicating the in vivo applicability of the nanofibers of the present invention.

In addition, the biodegradability was measured to increase with the increase of % (w/v) of MA-HA-(MEDN)-NONOates, that is, with the increase of the content of HA in the nanofibers.

Experimental Example 5: Cytotoxicity Assay

Figure 8:
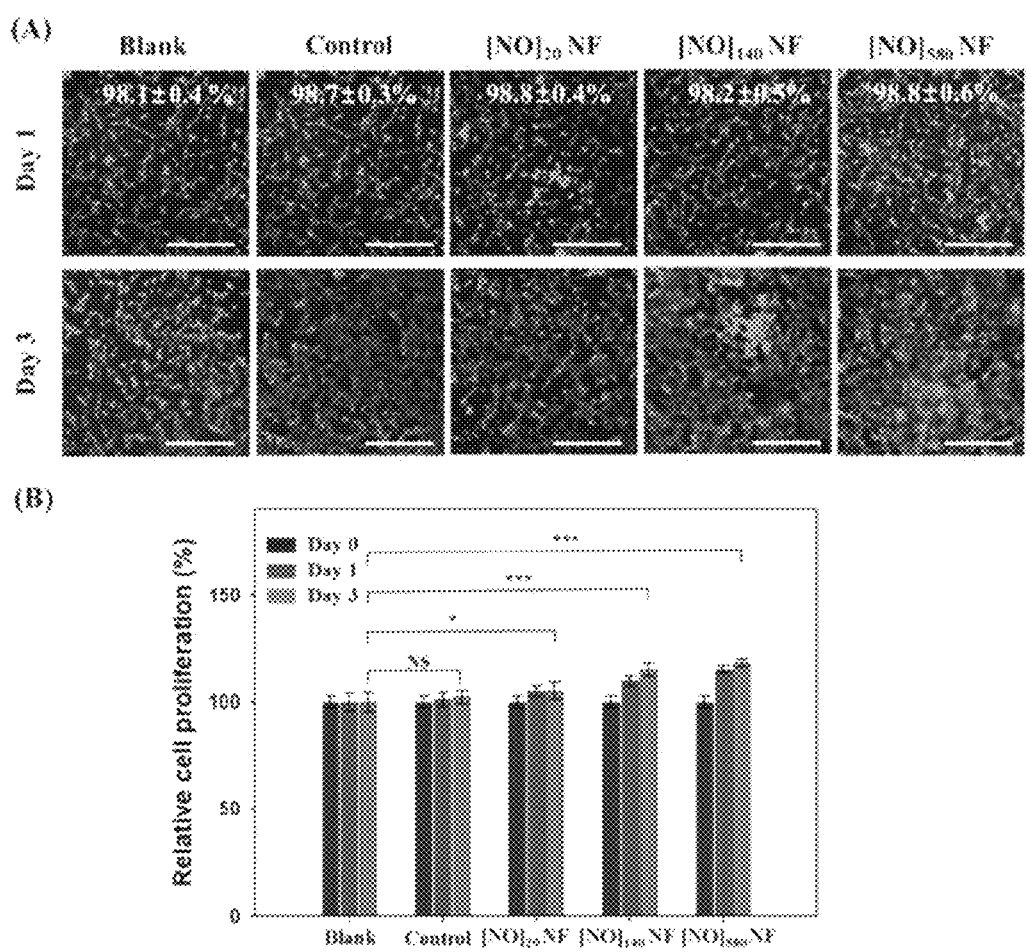
FIG. 8 shows microscopic images for assaying cytotoxicity of nanofibers for storing and releasing nitric oxide according to embodiments (A), together with the cell proliferation assay results thereof (B)

Nanofibers prepared by 7% (w/v) MA-HA-(MEDN)-NONOates (MA-HA:(MEDN)-NONOates=1:2, 1:5, 1:7) were used for in vitro cytotoxicity assay. As shown in Table 1, average nitric oxide payloads of V % (w/v) MA-HA:(MEDM)-NONOates=1:2, 1:5, and 1:7 based nanofibers were 20, 140, and 580 nmol·mg$^{-1}$, respectively. In FIG. 8, the nanofibers were denoted [NO]$_{20}$NF, [NO]$_{140}$NF, and [NO]$_{580}$NF, respectively. For example, [NO]$_{20}$NF stands for 20 nmol nitric oxide release amounts per 1 mg of nanofiber.

We evaluated the cytotoxicity of nitric oxide-releasing nanofibers for promising therapeutic application against NIH/3T3 fibroblasts as a model cell line due to their significant role in wound healing. To evaluate the toxicity of the nanofiber itself, MA-HA-(MEDN) incorporated nanofiber as a positive control was prepared. As another positive control (blank), a cell monolayer without any nanofiber contact was also prepared.

As shown in the upper panels of FIG. 8(A), the cell viability of the blank, control, [NO]$_{20}$NF, [NO]$_{140}$NF, and [NO]$_{580}$NF at day 1 was determined to be 98.1, 98.7, 98.8, 98.2, and 98.8%, respectively. In the lower panels of FIG. 8(A), live/dead images showed the faster proliferation with more spindle shapes than those of control and blank group when fibroblasts cultured for 3 days with nitric oxide-releasing nanofibers. By chemical conjugation of HA with methacryl and secondary amine containing NONOates groups, the NONOates and crosslinking chemical were not simply physically entrapped in the nanofiber network but were actually chemically anchored in the network. Meanwhile, NONOates breakdown and nitric oxide release from the nanofibers under physiological milieu whereas other chemicals would not leach out easily from the nanofiber. Therefore, nitric oxide-releasing nanofibers and nanofiber-forming chemistry were not toxic to the cells, reducing the potential toxicity issue for any in vivo application.

Experimental Example 6: Cell Proliferation Assay

It is well known that nitric oxide is involved in wound healing. In this Experimental Example, a cell proliferation assay was made with the assumption that the nitric oxide-releasing nanofibers were effective for the proliferation of fibroblasts. Briefly, quantitative effects of the nanofibers on fibroblast proliferation were investigated by WST-8 assay. As shown in FIG. 8(B), fibroblasts proliferations for 3 days of [NO]$_{20}$NF, [NO]$_{140}$ NF, and [NO]$_{580}$ NF were increased up to 5.3%, 15.2%, and 18.5% compared to that of blank group, respectively. In contrast, control group showed negligible effects on cell proliferation. These results indicate that nitric oxide released from the nanofibers can effectively provide a proper environment for fibroblast proliferation.

Experimental Example 7: Cell Motility Assay

Figure 9:
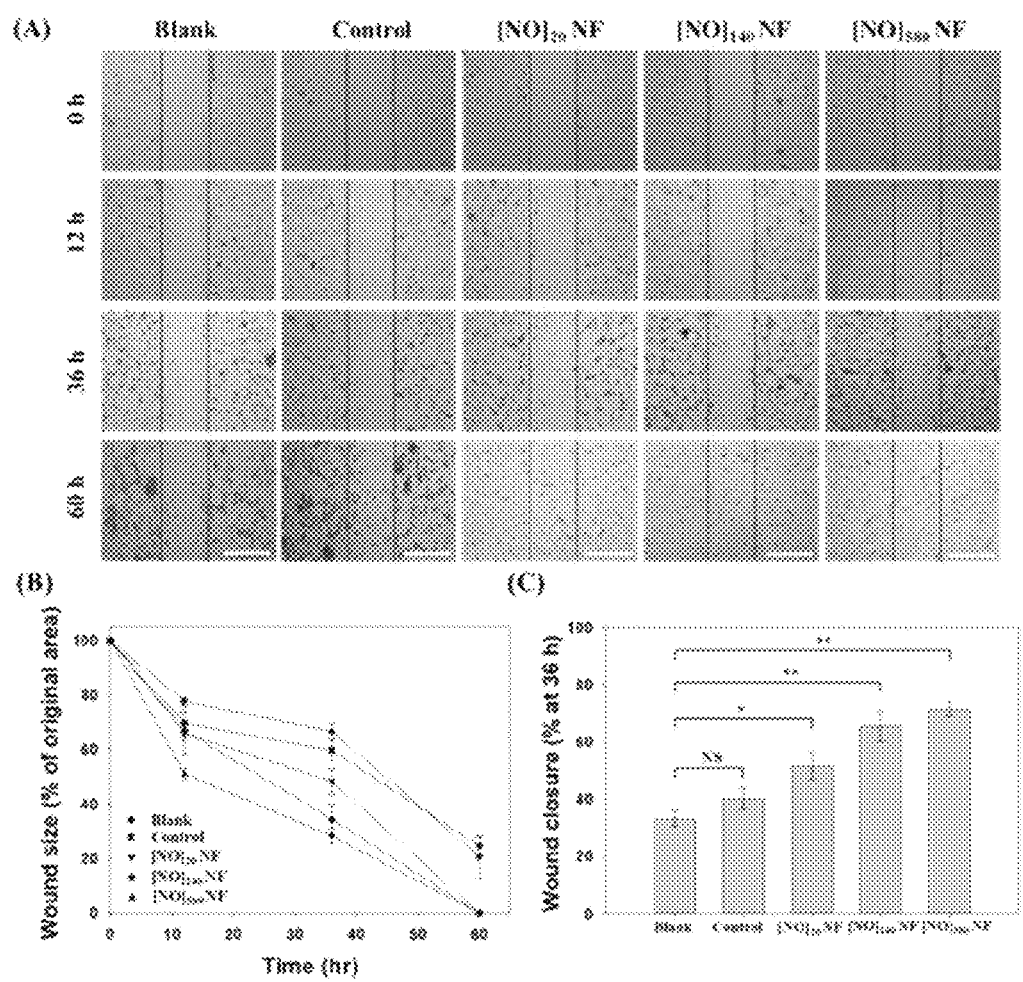
FIG. 9 shows optical images for wound healing effects of nanofibers for storing and releasing nitric oxide (A), together with the quantitative analysis results of the images (B and C)

In order to study the therapeutic potential of the nanofibers according to various embodiments of the present disclosure, an in vitro scratch test was performed. With reference to the images of the uppermost row in FIG. 9(A), a monolayer of fibroblasts was scratched to establish in vitro wound healing models (single line wound site). The scratched fibroblasts were cultured for 12 hours in the presence or absence of nitric oxide-releasing nanofibers. After 12 hours culture, relative scratched areas of [NO]$_{20}$ NF, [NO]$_{140}$ NF, and [NO]$_{580}$ NF-treated fibroblasts repopulated 34%, 33%, and 49%, respectively. In contrast, as shown in FIG. 9(B), untreated (blank) or only nanofiber (control)-treated fibroblasts repopulated only 22% and 29%. As shown in FIGS. 9(B) and 9(C), 36 hours after culture, [NO]$_{20}$ NF, [NO]$_{140}$ NF, and [NO]$_{580}$ NF-treated fibroblasts displayed significantly improved wound closure with 52, 65, and 72% compared to its original wound. Untreated and only nanofiber-treated fibroblasts showed somewhat lower wound closure effects with 33 and 40%, respectively. In addition, allowing the formation of a homogeneous monolayer of cells within 60 hours, all the nitric oxide-releasing nanofibers promoted fibroblastic proliferation. Thus, the nanofibers according to various embodiments of the present disclosure were found to provoke cell migration, thereby improving wound healing. Thus, the data indicate that the nanofibers have a therapeutic potential in would healing applications. In other words, various embodiments of the present disclosure can find applications in various regenerative medicine fields including burn treatment, renal transplantation, etc.

Experimental Example 8: Release Profile of Nitric Oxide Depending on Kind and Amount of Base Added to Polymer Precursor In step 5 for synthesis of nanofibers, the polymer precursor for electrospinning was prepared as follows and was assayed for nitric oxide storage and release profiles.

(1) Assay for nitric oxide storage and release profiles depending on molar concentration of $NH_4OH$ Upon preparation of the polymer precursor, $NH_4OH$ was added as a base at various molar concentrations. Subsequently, the electrospun nanofibers were assayed for nitric oxide release profile.

Figure 10:
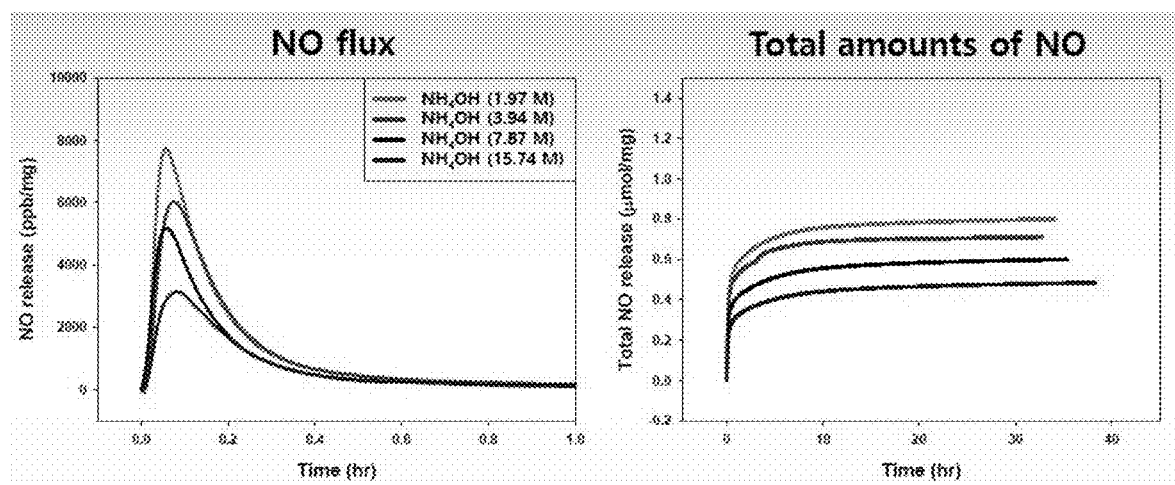
FIG. 10 shows storage and release profiles of the nanofibers according to molar concentrations of $NH_4OH$.

The results are given in Table 2, below and FIG. 10. As understood from the data, both the total amount of NO release and the maximum flux of NO increased with decreasing of molar concentration of $NH_4OH$.

TABLE 2

| | t[NO] ($\mu mol \cdot mg^{-1}$) | $t_{1/2}$ (min) | $[NO]_m$ (ppb · $mg^{-1}$) | $t_m$ (min) | $t_d$ (hr) |
|---|---|---|---|---|---|
| $NH_4OH$(1.97M) | 0.80 | 13 | 7,763 | 4 | 34.1 |
| $NH_4OH$(3.94M) | 0.71 | 14 | 6,053 | 5 | 32.7 |
| $NH_4OH$(7.87M) | 0.60 | 15 | 5,207 | 4 | 35.3 |
| $NH_4OH$(15.74M) | 0.48 | 19 | 3,148 | 5 | 38.3 | t[NO]: Total amount of NO release
$t_{1/2}$: Half life time of NO
$[NO]_m$: Maximum flux of NO
$t_m$: Time until maximum flux
$t_d$: Duration time of NO (2) Assay for nitric oxide storage and release profiles depending on molar concentration of NaOMe Upon preparation of the polymer precursor, NaOMe was added as a base at various molar concentrations. Subsequently, the electrospun nanofibers were assayed for nitric oxide release profile.

Figure 11:
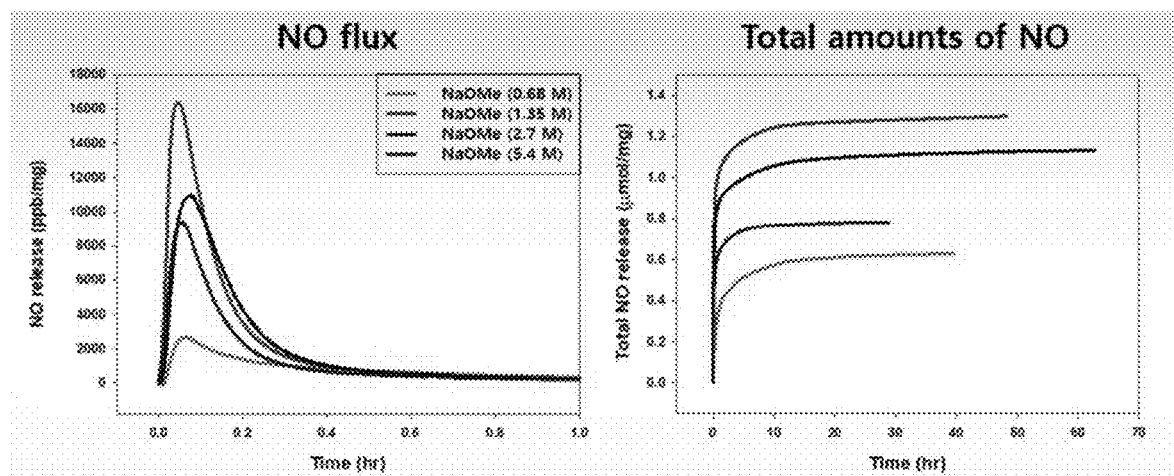
FIG. 11 shows storage and release profiles of the nanofibers according to molar concentrations of NaOMe.

As understood from the data of Table 3 and FIG. 11, when the molar concentration of NaOMe was 1.35 M, the total amount of NO peaked to 1.30 $\mu mol \cdot mg^{-1}$, which is about two folds higher than that for $NH_4OH$ (7.87 M), indicating that the nanofibers from the NaOMe-added polymer precursor is very high in nitric oxide storage capacity. In addition, the total amount of NO was observed to increase two or more folds with increasing of the molar concentration of NaOMe from 0.68 M to 1.35 M, but decrease as the molar concentration of NaOMe increases to 2.7 M and 5.4 M. Meanwhile, when NaOMe was used at the molar concentration of 2.7 M, the duration time of nitric oxide release was 63.2 hours, which was the longest. This molar concentration is considered to be useful for the long duration time of NO release.

TABLE 3

| | t[NO] ($\mu mol \cdot mg^{-1}$) | $t_{1/2}$ (min) | $[NO]_m$ (ppb · $mg^{-1}$) | $t_m$ (min) | $t_d$ (hr) |
|---|---|---|---|---|---|
| NaOMe(0.68M) | 0.62 | 42 | 2,583 | 4 | 39.5 |
| NaOMe(1.35M) | 1.30 | 9 | 16,422 | 3 | 48.3 |
| NaOMe(2.7M) | 1.13 | 11 | 10,898 | 5 | 63.2 |
| NaOMe(5.4M) | 0.78 | 9 | 9,411 | 3 | 29.0 |

(3) Assay for nitric oxide storage and release profiles depending on molar concentration of NaOEt Upon preparation of the polymer precursor, NaOEt was added as a base at various molar concentrations. Subsequently, the electrospun nanofibers were assayed for nitric oxide release profile.

Figure 12:
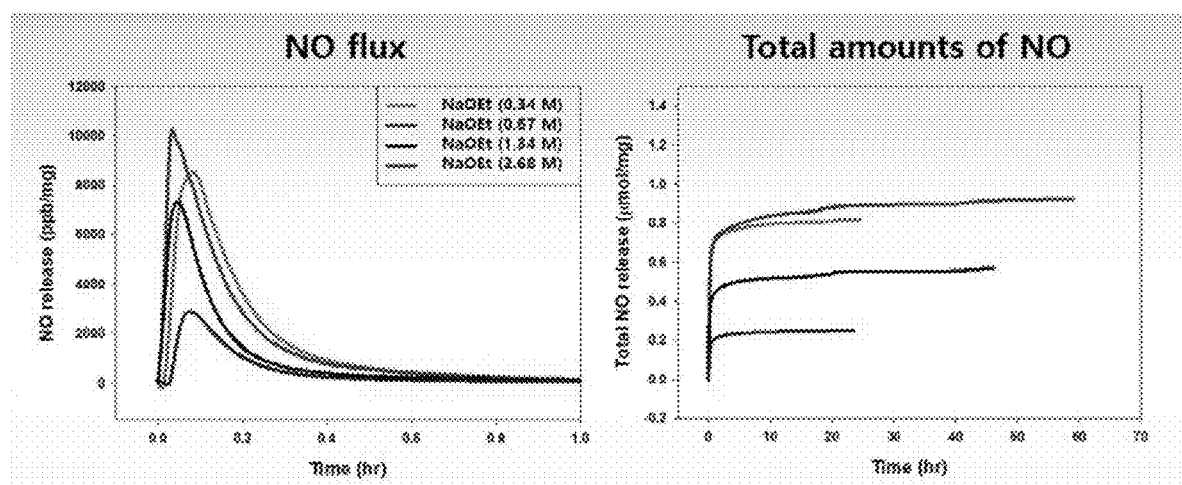
FIG. 12 shows storage and release profiles of the nanofibers according to molar concentrations of NaOEt.

As understood from the data of Table 4 and FIG. 12, when NaOEt was used at the molar concentration of 0.67 M, the total amount of NO release peaked to 0.92 $\mu mol \cdot mg^{-1}$. The total amount of NO release was observed to increase with increasing of the molar concentration of NaOEt from 0.34 M to 0.67 M, but decrease as the molar concentration of NaOEt increases to 1.34 M and 2.68 M.

TABLE 4

| | t[NO] ($\mu mol \cdot mg^{-1}$) | $t_{1/2}$ (min) | $[NO]_m$ (ppb · $mg^{-1}$) | $t_m$ (min) | $t_d$ (hr) |
|---|---|---|---|---|---|
| NaOEt(0.34M) | 0.82 | 10 | 8,557 | 5 | 24.4 |
| NaOEt(0.67M) | 0.92 | 10 | 10,063 | 2 | 59.0 |
| NaOEt(1.34M) | 0.57 | 8 | 7,385 | 3 | 46.1 |
| NaOEt(2.68M) | 0.25 | 10 | 2,880 | 4 | 23.4 |

(4) Assay for nitric oxide storage and release profiles depending on molar concentration of NaOPr Upon preparation of the polymer precursor, NaOPr was added as a base at various molar concentrations. Subsequently, the electrospun nanofibers were assayed for nitric oxide release profile.

Figure 13:
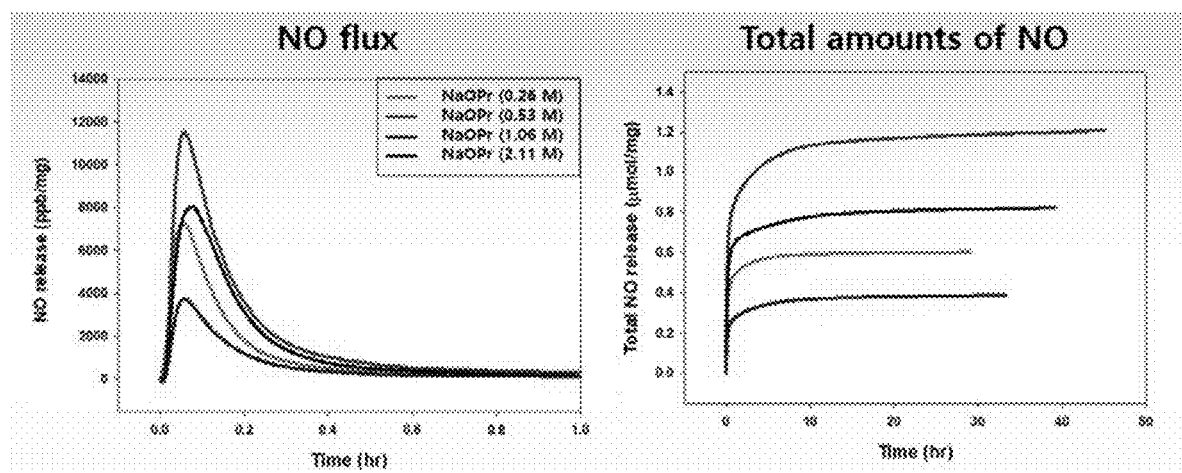
FIG. 13 shows storage and release profiles of the nanofibers according to molar concentrations of NaOPr.

As understood from the data of Table 5 and FIG. 13, when the molar concentration of NaOPr was 0.53 M, the total amount of nitric oxide peaked to 1.21 $\mu mol \cdot mg^{-1}$. The total amount of NO was observed to increase two or more folds with increasing of the molar concentration of NaOPr from 0.28 M to 0.53 M, but decrease as the molar concentration of NaOPr increases to 1.06 M and 2.11 M.

TABLE 5

| | t[NO] ($\mu mol \cdot mg^{-1}$) | $t_{1/2}$ (min) | $[NO]_m$ (ppb · $mg^{-1}$) | $t_m$ (min) | $t_d$ (hr) |
|---|---|---|---|---|---|
| NaOPr(0.28M) | 0.60 | 9 | 7,260 | 3 | 29.1 |
| NaOPr(0.53M) | 1.21 | 14 | 10,925 | 4 | 45.2 |
| NaOPr(1.06M) | 0.82 | 11 | 8,014 | 5 | 39.2 |
| NaOPr(2.11M) | 0.38 | 13 | 3,776 | 4 | 33.3 |

The data obtained in Experimental Example 8 indicates that the base contained in the polymer precursor can be applied according to the amounts and duration times of nitric oxide at a target concentration.

The features, structures, effects, and the like described in the above-described embodiments include at least one embodiment of the present disclosure, but the present disclosure is not limited only to one embodiment. Further, the features, structures, effects, and the like illustrated in each embodiment may be combined or modified to other embodiments by those skilled in the art. Therefore, contents related to the combination or the modification should be interpreted to be included in the scope of the disclosure.

In addition, while the present disclosure has been particularly described with reference to exemplary embodiments, the present disclosure is not limited thereto. It will be understood by those skilled in the art that various modifications and applications, which are not illustrated in the above, may be made without departing from the spirit and scope of the present disclosure. For example, each component illustrated in the embodiments may be modified and made. It should be interpreted that differences related to these modifications and applications are included in the scope of the invention defined in the appended claims.

What is claimed is:

1. A polymer, comprising:
   a plurality of repeat units selected from the repeat units of hyaluronic acid, starch, chitin, cellulose, alginate, heparin, and chitosan,
   wherein at least one hydroxyl group of the at least one repeat unit of starch, chitin, cellulose, or chitosan is converted into to a carboxyl group; and
   wherein at least one carboxyl group of the at least one repeat unit of alginate or heparin is converted into a hydroxyl groups; and
   wherein:
   at least one repeat unit of the plurality comprises a nitric oxide-releasing compound conjugated to a carboxyl group, said nitric oxide-releasing compound comprising an NO donor, and
   at least one repeat unit of the plurality comprises a photopolymerizable functional group conjugated to a hydroxyl group.

2. The polymer of claim 1, wherein the NO donor comprises at least one selected from the group consisting of organic nitrites, organic nitrates, nitrosothiols, C-nitroso compounds, N-hydroxyl nitrosamine, diazetine dioxides, oxatriazole-5-imine, N-nitrosamines, sydnonimines, oximes, hydroxylamines, N-hydroxyguanidines, hydroxyurea, nitrosiamine, N-hydroxyl nitrosamines, NO-metal complexes, and N-diazeniumdiolates (NONOates).

3. The polymer of claim 1, wherein the nitric oxide-releasing compound comprises a NO donor modified from an amine compound which comprises at least one selected from the group consisting of N-methylethylendiamine (N-MEDN), N-ethylethylenediamine (N-EEDN), N-isopropylethylenediamine (N-IPED), N-isopropyl-1,3-propanediamine (N-IPPDN), and N-benzylethylenediamine (N-BEDN).

4. The polymer of claim 1, wherein the nitric oxide-releasing compound comprises at least one selected from the group consisting of (MEDN)-NONOates modified from N-MEDN, (EEDN)-NONOates modified from N-EEDN, (IPED)-NONOates modified from N-IPED, (IPPDN)-NONOates modified from N-IPPDN, and (BEDN)-NONOates modified from N-BEDN.

5. The polymer of claim 1, wherein the photopolymerizable functional group comprises at least one selected from the group consisting of a methacrylate, ethacrylate, crotonate, cinnamate, vinyl ether, vinyl ester, ethenylarylene, dicyclopentadienyl, norbornenyl, isoprenyl, isopropenyl, allyl, or butenyl group; an ethenylarylene ether, dicyclopentadienyl ether, norbornenyl ether, isoprenyl ether, isopropenyl ether, allyl ether or butenyl ether group; and an ethenylarylene ester, dicyclopentadienyl ester, norbornenyl ester, isoprenyl ester, isopropenyl ester, allyl ester, and butenyl ester, or glycidyl methacrylate group.

6. The polymer of claim 1, wherein the plurality of the repeat units are the repeat units of hyaluronic acid.

7. The polymer of claim 1, wherein the plurality of the repeat units are the repeat units of starch, chitin, cellulose, or chitosan.

8. The polymer of claim 1, wherein the the repeat units are the repeat units of alginate or heparin.

9. A nanofiber for storing and transferring nitric oxide, the nanofiber comprising:
   a polymer, comprising:
   a plurality of repeat units selected from the repeat units of hyaluronic acid, starch, chitin, cellulose, alginate, heparin, and chitosan,
   wherein at least one hydroxyl group of the at least one repeat unit of starch, chitin, cellulose, or chitosan is converted into to a carboxyl group; and
   wherein at least one carboxyl group of the at least one repeat unit of alginate or heparin is converted into a hydroxyl group; and
   wherein:
   at least one repeat unit of the plurality comprises a nitric oxide-releasing compound conjugated to a carboxyl group, said nitric oxide-releasing compound comprising an NO donor, and
   at least one repeat unit of the plurality comprises a photopolymerizable functional group conjugated to a hydroxyl group.

* * * * *